US006985664B2

(12) United States Patent
Caracci et al.

(10) Patent No.: US 6,985,664 B2
(45) Date of Patent: Jan. 10, 2006

(54) SUBSTRATE INDEX MODIFICATION FOR INCREASING THE SENSITIVITY OF GRATING-COUPLED WAVEGUIDES

(75) Inventors: Stephen J. Caracci, Elmira, NY (US); Mircea Despa, Horseheads, NY (US); Eric J. Mozdy, Elmira, NY (US); Mark D. Salik, Paris (FR)

(73) Assignee: Corning Incorporated, Corning, NY (US)

( * ) Notice: Subject to any disclaimer, the term of this patent is extended or adjusted under 35 U.S.C. 154(b) by 73 days.

(21) Appl. No.: 10/632,276

(22) Filed: Aug. 1, 2003

(65) Prior Publication Data

US 2005/0025421 A1 Feb. 3, 2005

(51) Int. Cl.
G02B 6/10 (2006.01)
(52) U.S. Cl. .......................... 385/130; 385/10; 385/37; 385/14
(58) Field of Classification Search ................. 385/10, 385/37, 14, 27, 39, 124, 123, 129, 130
See application file for complete search history.

(56) References Cited

U.S. PATENT DOCUMENTS

| | | | |
|---|---|---|---|
| 3,806,226 A | * | 4/1974 | Tien ............................ 385/43 |
| 3,814,498 A | * | 6/1974 | Tomlinson et al. ........... 385/37 |
| 3,839,067 A | * | 10/1974 | Sosnowski et al. .......... 427/164 |
| 4,815,843 A | | 3/1989 | Tiefenthaler et al. ....... 356/128 |
| 5,369,722 A | | 11/1994 | Heming et al. ............. 385/130 |
| 5,684,900 A | * | 11/1997 | Nishiwaki et al. ............ 385/31 |
| 5,738,825 A | | 4/1998 | Rudigier et al. ......... 422/82.11 |
| 5,832,165 A | * | 11/1998 | Reichert et al. ............ 385/130 |
| 2002/0034457 A1 | * | 3/2002 | Reichert et al. ......... 422/82.11 |
| 2002/0109100 A1 | | 8/2002 | Jackson, III et al. ..... 250/458.1 |
| 2002/0127565 A1 | | 9/2002 | Cunningham et al. ......... 435/6 |
| 2002/0168295 A1 | | 11/2002 | Cunningham et al. ... 422/82.05 |
| 2003/0017580 A1 | | 1/2003 | Cunningham et al. ... 435/287.2 |
| 2003/0017581 A1 | | 1/2003 | Li et al. .................. 435/287.2 |
| 2003/0023014 A1 | | 1/2003 | Smith et al. ................. 526/242 |
| 2003/0026891 A1 | | 2/2003 | Qiu et al. ...................... 427/58 |
| 2003/0027327 A1 | | 2/2003 | Cunningham et al. ... 435/287.2 |
| 2003/0027328 A1 | | 2/2003 | Cunningham et al. ... 435/287.2 |

(Continued)

FOREIGN PATENT DOCUMENTS

DE          4104392          8/1992

(Continued)

OTHER PUBLICATIONS

N.H. Fontaine et al., "Variable-angle internal-reflection Raman spectroscopy for depth-resolved vibrational characterization of polymer thin films", Physical Review B, vol. 57, No. 7, Feb. 15, 1998, p. 3807-3810.

(Continued)

*Primary Examiner*—K. Cyrus Kianni
(74) *Attorney, Agent, or Firm*—William J. Tucker; Thomas R. Beall

(57) ABSTRACT

A grating-coupled waveguide (GCW) and a method are described herein that can be used to detect the presence of a biological substance (e.g., cell, drug, chemical compound) in a sensing region of the GCW. The GCW includes a substrate, a diffraction grating and a waveguide film that has a higher index of refraction than the substrate which has an index of refraction ≦1.5. The relatively low-index substrate effectively increases the sensitivity of the GCW by causing the waveguide mode to shift towards a biological substance located in a sensing region above the waveguide film, thereby increasing the field strength of the mode's evanescent tail in this region. In one embodiment, an array of the GCWs are incorporated within the wells of a microplate.

12 Claims, 8 Drawing Sheets

U.S. PATENT DOCUMENTS

| | | |
|---|---|---|
| 2003/0032039 A1 | 2/2003 | Cunningham et al. .......... 435/6 |
| 2003/0059855 A1 | 3/2003 | Cunningham et al. ....... 435/7.9 |
| 2003/0068657 A1 | 4/2003 | Lin et al. ...................... 435/7.9 |
| 2003/0077660 A1 | 4/2003 | Pien et al. .................... 435/7.1 |
| 2003/0092075 A1 | 5/2003 | Pepper ........................ 435/7.9 |
| 2003/0113766 A1 | 6/2003 | Pepper et al. ................... 435/6 |
| 2004/0038386 A1 * | 2/2004 | Zesch et al. ............. 435/287.2 |
| 2004/0132172 A1 | 7/2004 | Cunningham et al. ... 435/287.2 |
| 2004/0132214 A1 | 7/2004 | Lin et al. .................... 436/518 |
| 2004/0151626 A1 | 8/2004 | Cunningham et al. ........ 422/58 |
| 2004/0223881 A1 | 11/2004 | Cunningham et al. ... 422/82.05 |

FOREIGN PATENT DOCUMENTS

| | | |
|---|---|---|
| EP | 1 031 828 | 8/2000 |
| WO | WO 90/08318 | 7/1990 |
| WO | WO 02/35214 | 5/2002 |
| WO | WO 03/021313 | 3/2003 |

OTHER PUBLICATIONS

A. Grandenburg et al., "Grating Couplers as chemical sensors: a new optical configuration", Sensors and Actuators B, 17 (1993), p. 35-40.

K. Tiefenthaler et al., "Sensitivity of grating couplers as integrated-optical chemical sensors", J. Opt. Soc. Am. B, vol. 6, No. 2, Feb. 1989, p. 209-220.

W. Lukosz, "Integrated optical chemical and direct biochemical sensors", Sensors and Actuators B, 29 (1995), pp. 37-50.

K. Tiefenthaler et al., "Integrated optical switches and gas sensors", Optics Letters, Apr. 1984, vol. 10, No. 4, pp. 137-139.

W. Lukosz et al., Sensitivity of integrated optical grating and prism couplers as (Bio)Chemical Sensors, Sensors & Actuators, vol. 15, 1988, No. 3, Lausanne, Switzerland, pp. 273-284.

Ph. M. Nellen et al., "Integrated optical input grating couplers as biochemical sensors", Sensors & Actuators, vol. 15, No. 3, 1988, Lausanne, Switzerland, pp. 285-295.

R.E. Kunz et al., "Finite grating depth effects for integrated optical sensors with high sensitivity", Biosensors & Bioelectronics, vol. 11, No. 6/7, pp. 653-667.

B. Cunningham et al., Colorimetric resonant reflection as a direct biochemical assay technique, Sensors & Actuators B, vol. 81, 2002, pp. 316-328.

W. Lukosz, "Principles and sensitivities of integrated optical and surface plasmon sensors for direct affinity sensing and immunosensing", Biosensors & Bioelectronics, vol. 6, 1991, pp. 215-225.

W. Lukosz, "Integrated optical chemical and direct biochemical sensors", Sensors & Actuators B, vol. 29, 1995, pp. 37-50.

O. Parriaux et al., "Sensitivity optimization of a grating coupled evanescent wave immunosensor", Sensors & Actuators B, vol. 29, 1995, pp. 289-292.

* cited by examiner

SUBSTRATE INDEX MODIFICATION FOR INCREASING THE SENSITIVITY OF GRATING-COUPLED WAVEGUIDES

BACKGROUND OF THE INVENTION

1. Field of the Invention

The present invention relates in general to a grating-coupled waveguide and, in particular, to a grating-coupled waveguide that includes a substrate, a diffraction grating and a waveguide film that has a higher index of refraction than the substrate which has an index of refraction $\leq 1.5$.

2. Description of Related Art

Grating-coupled waveguides (GCWs) can provide a very narrow spectral response to incident light emitted from an optical interrogation system, and have therefore been used in a wide variety of applications including optical filters, laser cavity mirrors and biosensors (for example). In the biosensing application, the optical interrogation system monitors variations in the optical response of the GCW as a biological substance is brought into contact with the GCW, thereby altering the monitored optical response of the GCW through material binding, adsorption etc. . . . In this manner, the GCW enables direct optical monitoring of biological events, allowing label-free assays where the expense and experimental perturbations of fluorescent dyes are completely avoided. In order to produce competing functionality however, GCWs need to be optimized in terms of sensitivity to detect biological substances. The present invention relates to a design modification of a traditional GCW that enables one to make and use a highly sensitive GCW.

BRIEF DESCRIPTION OF THE INVENTION

The present invention includes a GCW and a method for using the GCW to detect the presence of a biological substance (e.g., cell, drug, chemical compound) in a sensing region of the GCW. The GCW includes a substrate, a diffraction grating and a waveguide film that has a higher index of refraction than the substrate which has an index of refraction $\leq 1.5$. The relatively low-index substrate effectively increases the sensitivity of the GCW by causing the waveguide mode to shift towards a biological substance located in a sensing region above the waveguide film, thereby increasing the field strength of the mode's evanescent tail in this region. In one embodiment, an array of the GCWs are incorporated within the wells of a microplate.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
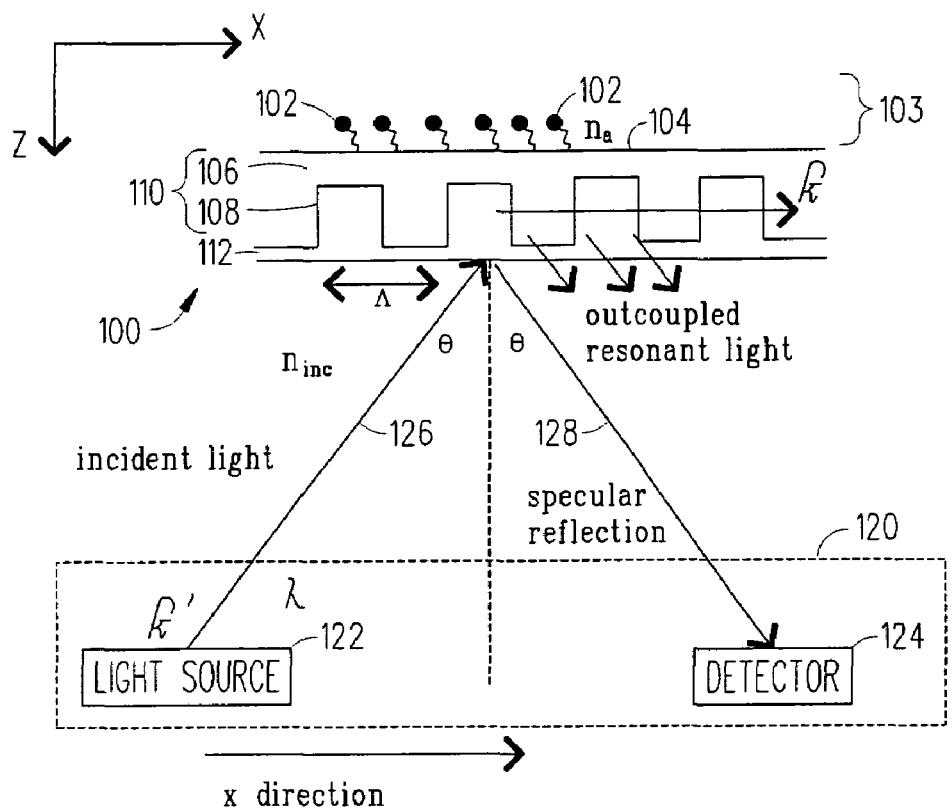
FIG. 1 is a diagram of the basic components of a GCW and optical interrogation system in accordance with the present invention.

Referring to FIG. 1, there is shown a diagram of the basic components of a GCW 100 and an optical interrogation system 120 in accordance with the present invention. Basically, the GCW 100 makes use of the refractive and coupling properties of light 126 emitted from the optical interrogation system 120 and light 128 reflected back into the optical interrogation system 120 to enable label-free detection of a biological substance 102 (e.g., cell, molecule, protein, drug, chemical compound, nucleic acid, peptide, carbohydrate) on the superstrate 103 (sensing region) of the GCW 100. The optical interrogation system 120 includes one or more light sources 122 (e.g., laser, diodes) and one or more detectors 124 (e.g., spectrometers, CCD cameras or other optical detectors).

The GCW 100 includes a thin (~100 nm) layer of material 106 (e.g., waveguide film 106) deposited on a substrate 112 either before or after the fabrication of a diffraction grating 108 which together form a waveguide 110. The diffraction grating 108 is formed within the substrate 112 or waveguide film 106 by embossing, holography, or other methods. The diffraction grating 108 can thereby be located above, below, or even within the waveguide film 106. Moreover, the diffraction grating 108 need not be in direct physical contact with a waveguide film 106, simply near enough to cause optical influence on the waveguide mode. Furthermore, due to effective-index waveguiding, the diffraction grating 108 itself can be fabricated with appropriately high enough index to serve as the waveguide itself without the need for an additional deposition of an waveguide film 106. The waveguide film 106 is preferably made of a metal-oxide based material such as $Ta_2O_5$, $TiO_2$, $TiO_2$—$SiO_2$, $HfO_2$, $ZrO_2$, $Al_2O_3$, $Si_3N_4$, HfON, SiON, scandium oxides or mixtures thereof. As shown, the diffraction grating 108 is formed within a substrate 112 by embossing, holography, or other methods and then the thin waveguide film 106 having a higher refractive index is coated on top of the diffraction grating 108. A detailed discussion is provided below about some of the different low-index materials that can be used to make the substrate 112.

The biological substance 102 which may be located within a bulk fluid is deposited on the superstrate 103 (sensing region) of the GCW 100 and it is the presence of this biological substance 102 that alters the index of refraction at the surface 104 of the GCW 100. Thus, to detect the biological substance 102, the GCW 100 is probed with a light beam 126 emitted from the light source 122 and then a reflected light beam 128 received at the detector 124 is analyzed to determine if there are any changes (~1 part per million) in the refractive index caused by the presence of the biological substance 102. In one embodiment, the top surface 104 may be coated with biochemical compounds (not shown) that only allow surface attachment of specific complementary biological substances 102 which enables an GCW 100 to be created that is both highly sensitive and highly specific. In this way, the optical interrogation system 120 and GCWs 100 may be used to detect a wide variety of biological substances 102 and if the GCWs 100 are arranged in arrays they may be used to enable high throughput drug or chemical screening studies.

The sensitivity of the GCW 100 may be best understood by analyzing the structure of the diffraction grating 108 and the waveguide 110. The light beam 126 shone on the diffraction grating 108 can only be coupled into the waveguide 110 if its wave vector satisfies the following resonant condition as shown in equation no. 1:

$$k'_x = k_x - \kappa \qquad [1]$$

where $k_x'$ is the x-component of the incident wave vector, $k_x$ is the guided mode wave vector, and $\kappa$ is the grating vector. The grating vector $\kappa$ is defined as a vector having a direction perpendicular to the lines of the diffraction grating 108 and a magnitude given by $2\pi/\Lambda$ where $\Lambda$ is the grating period (pitch) (see FIG. 1). This expression may also be written in terms of wavelength $\lambda$ and incident angle $\theta$ as shown in equation no. 2:

$$\frac{2\pi n_{inc}}{\lambda} \sin\theta = \frac{2\pi n_{eff}}{\lambda} - \frac{2\pi}{\Lambda} \qquad [2]$$

Where $\theta$ is the angle of incidence of the light beam 126, $n_{inc}$ is the index of refraction of the incident medium, $\lambda$ is the wavelength of the light 126, and $n_{eff}$ is the effective index of refraction of the waveguide 110. The effective index of the waveguide 110 is a weighted average of the indices of refraction that the optical waveguide mode field or fundamental mode "sees" as it propagates through the waveguide 110. The fundamental mode preferably has a spatial extent that is much wider than the waveguide 110 itself, the extent depending on the refractive index of the substrate 112. In particular, the fundamental mode has an evanescent wave/tail that extends into the superstrate 103 (sensing region) which "sees" any surface changes created when the biological substance 102 approaches or comes in contact with the top surface of the GCW 100.

Figure 2:
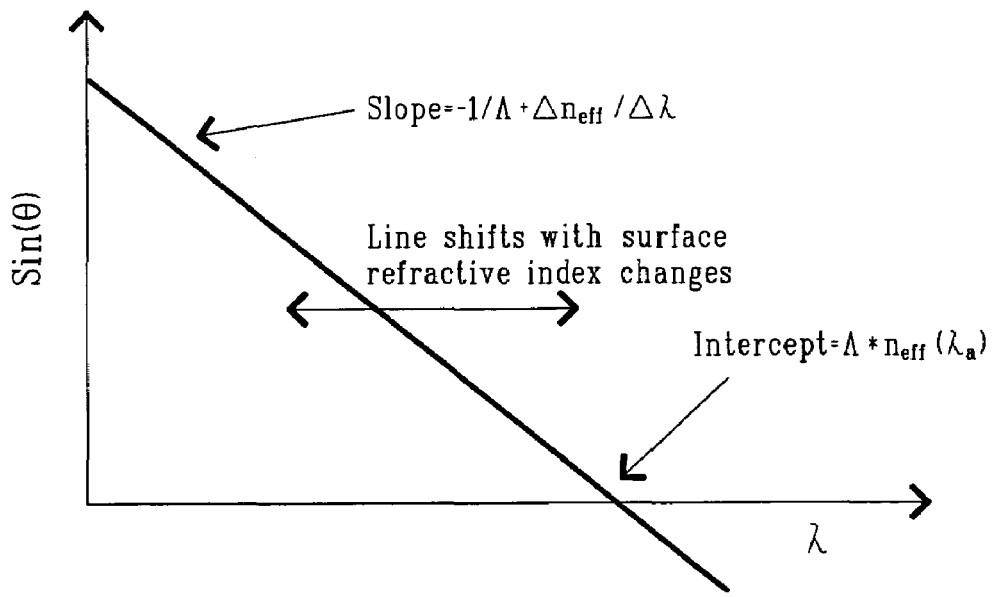
FIG. 2 is a graph that illustrates the relationship between the resonant angle and resonant wavelength of the GCW shown in FIG. 1.

The previous expression shown in equation no. 2 may be rewritten in the more convenient form shown in equation no. 3:

$$\sin\theta = n_{eff} - \frac{\lambda}{\Lambda} \qquad [3]$$

which is the equation of a line where $\sin\theta$ being the y axis, $\lambda$ being the x-axis, $\Delta n_{eff}$ the x-intercept, and $-1/\Lambda$ the slope. To obtain equation no. 3, $n_{inc}$ has been set to 1 so that it could be remove from this expression. This approximation is used since air (n~1.0003) is the most common incident medium. This relation is pictured in the graph shown in FIG. 2. When a biological substance 102 binds to the surface 104, the effective index of the waveguide 110 is altered which leads to the shifting the resonant wavelength or resonant angle of the GCW 100. This shifting can be seen as a shift of the x-intercept in the line shown in FIG. 2.

Figure 3:
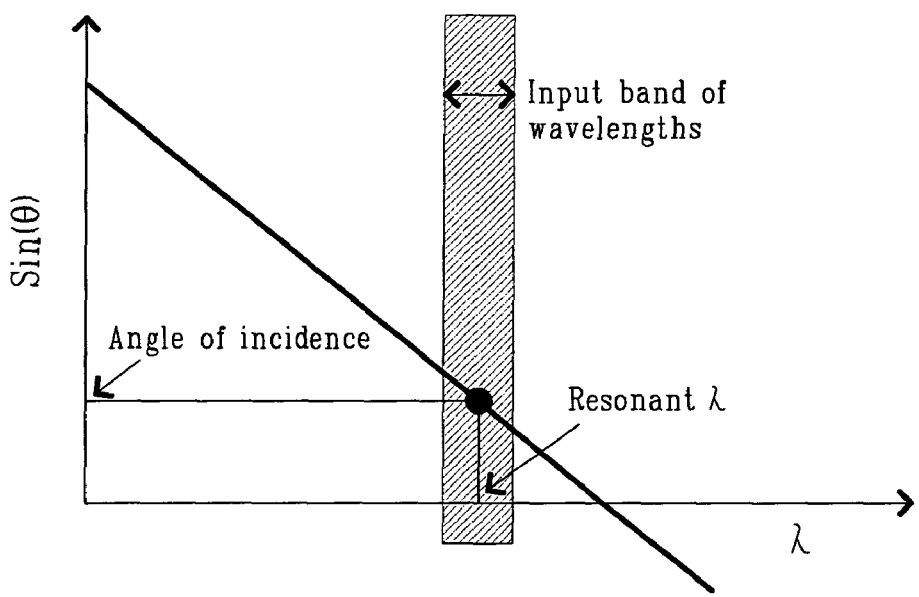
FIG. 3 is a graph used to help describe how a spectral interrogation approach can be used by the optical interrogation system to determine the resonant wavelength of the GCW shown in FIG. 1.
Figure 4:
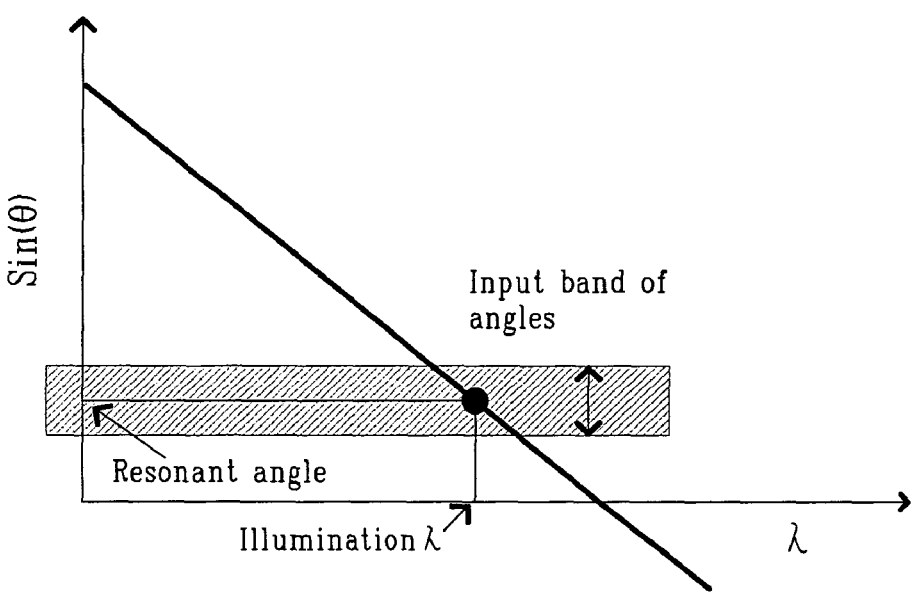
FIG. 4 is a graph used to help describe how an angular interrogation approach can be used by the optical interrogation system to determine the resonant angle of the GCW shown in FIG. 1.

The resonant condition (e.g., resonant wavelength or resonant angle) of such a GCW 100 may be interrogated to determine refractive index changes by observing the reflected light 128 from the GCW 100 (see FIG. 1). There are two different modes of operation for monitoring refractive index changes—spectral interrogation or angular interrogation. In spectral interrogation, a nominally collimated, broadband beam of light 126 is sent into the GCW 100 and the reflected light 128 is collected and monitored with a spectrometer 124 (for example). By observing the spectral location of the resonant wavelength (peak), one can monitor binding or refractive index changes on or near the surface 104 of the GCW 100. The spectral interrogation concept is graphically represented in the graph shown in FIG. 3. Conversely, in angular interrogation, a nominally single wavelength of light 126 is focused to create a range of illumination angles and directed into the GCW 100. The reflected light 128 is monitored with a CCD camera or other optical detector 124. By monitoring the position of the resonant angle reflected by the GCW 100, one can monitor binding or refractive index changes on or near the surface 104 of the GCW 100. The angular interrogation concept is graphically represented in the graph shown in FIG. 4.

Figure 5:
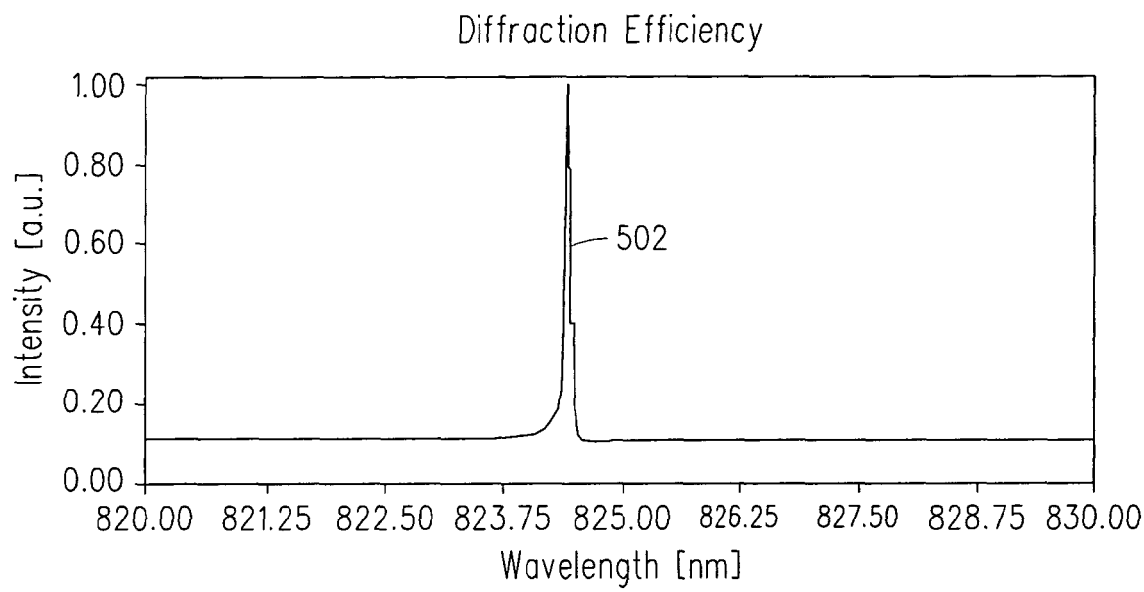
FIG. 5 (PRIOR ART) is a graph generated by GSOLVER that illustrates the resonant wavelength (reflection anomaly) of a traditional GCW having a substrate made from cyclic-olefin copolymer (COC) and a waveguide film made from $Ta_2O_5$.

To maintain simplicity and efficiency of operation, the GCWs 100 employed in biosensors are usually designed such that only the zeroth diffracted orders of the incident light 126 propagate in free space, while what would be the ±1 orders couple to the fundamental mode of the waveguide 110. The higher diffraction orders are avoided by designing a sub-wavelength diffraction grating 108 which has a grating pitch $\Lambda$ smaller than the desired operating wavelength $\lambda$ of the incident light 126. In this case, the coupling efficiency of the waveguide 110 is large since multiple orders do not remove power from the GCW 100. Moreover, since only the zeroth reflected and transmitted beams exist in free space, the GCW 100 can thereby produce nearly total reflection or transmission of the desired (anomalous) wavelength λ of the incident light 126. FIG. 5 shows a GSOLVER (rigorous coupled-wave analysis, or RCWA code) analysis of a traditional GCW 100 where the TE input light 126 angle is 3° and the reflected light beam 128 which is at 3° from the normal has a resonance 502 in the vicinity of 824 nm when the substance (water) in the superstrate 103 has an index of 1.33.

GCWs 100 are used in biosensing applications because they enable one to determine the location of the resonance angle/wavelength 502 and to calculate the refractive index of the superstrate 103. This is possible because the evanescent tail of the propagating fundamental mode in the waveguide 110 senses index changes in the superstrate 103 caused by the presence of the biological substance 102. The index change in the superstrate 103 changes the resonance condition of the GCW 100 according equation no. 1 and then the resonance 502 shifts to a new wavelength or angle location. The location of the shifted resonance indicates the current index of the superstrate 103 which indicates whether or not the biological substance 102 is in the superstrate 103 of the GCW 100. It has been shown that the resonance 502 can shift hundreds of nanometers for a unit change in the refractive index of the superstrate 103 (see FIG. 2). This shift is referred to as the wavelength or angular interrogation slope (WIS or AIS) of the GCW 100. Given the current technology associated with wavelength resolution of the detection instruments, noise levels, etc., this typically translates to detection limits of $10^{-6}$ RIU at the top surface 104 of the GCW 100. It is one purpose of this invention to relax the constraints on the instrumentation by increasing the WIS/AIS or sensitivity of the GCW 100 through a design modification of the substrate 112 in the GCW 100.

Figure 6:
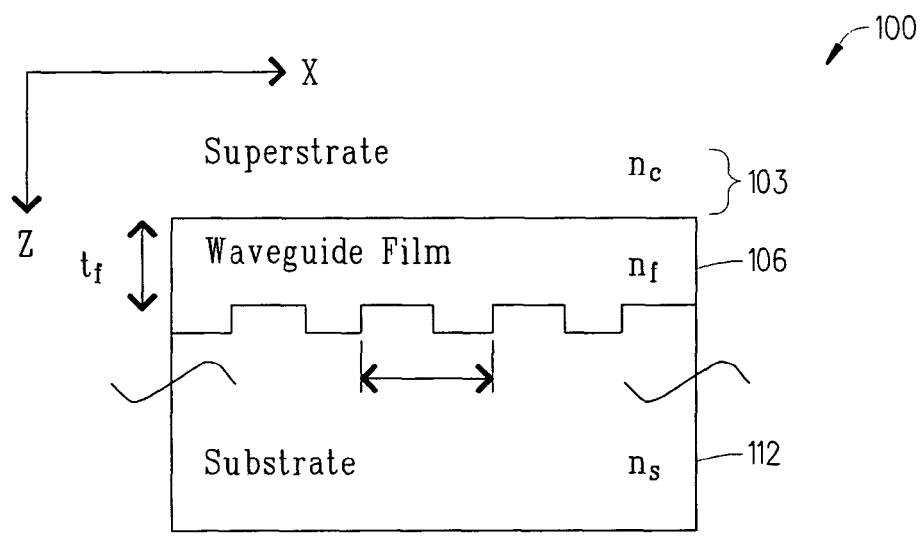
FIG. 6 is a simplified three-layer waveguide model of the GCW shown in FIG. 1.

To provide insight into the origin of the WIS/AIS of the GCW 100 a simplified 3-layer waveguide model is used as shown in FIG. 6. Since the sensitivity of the GCW 100 is primarily related to the overlap of the waveguide mode with the superstrate 103, this model is used to examine the guided mode structure versus the design of the GCW 100 which enables one to infer WIS/AIS. As shown in FIG. 6, the structure of the GCW 100 can be simplified into a three-layer structure: in the case where the diffraction grating 108 is a very small fraction (typically <5%) of the waveguide film 106 thickness, the grating 108 can be neglected altogether; or when the diffraction grating 108 is significant relative to the waveguide film 106, the central layer (waveguide film 106) is approximated using an effective index found by averaging the permittivities (square of index for lossless material) of the alternating sections of the diffraction grating 108. This may be a simple average due to the 50% duty cycle between the sections of the diffraction gratings 108. The substrate 112 and superstrate 103 are assumed to be infinite in the z-direction, and all layers 103, 106 and 112 are infinite in the x-direction. Any number of simple mode-solvers can be used to analyze this model of the GCW 100. The results of three different analyses are provided below with respect to FIGS. 7–11.

Figure 7:
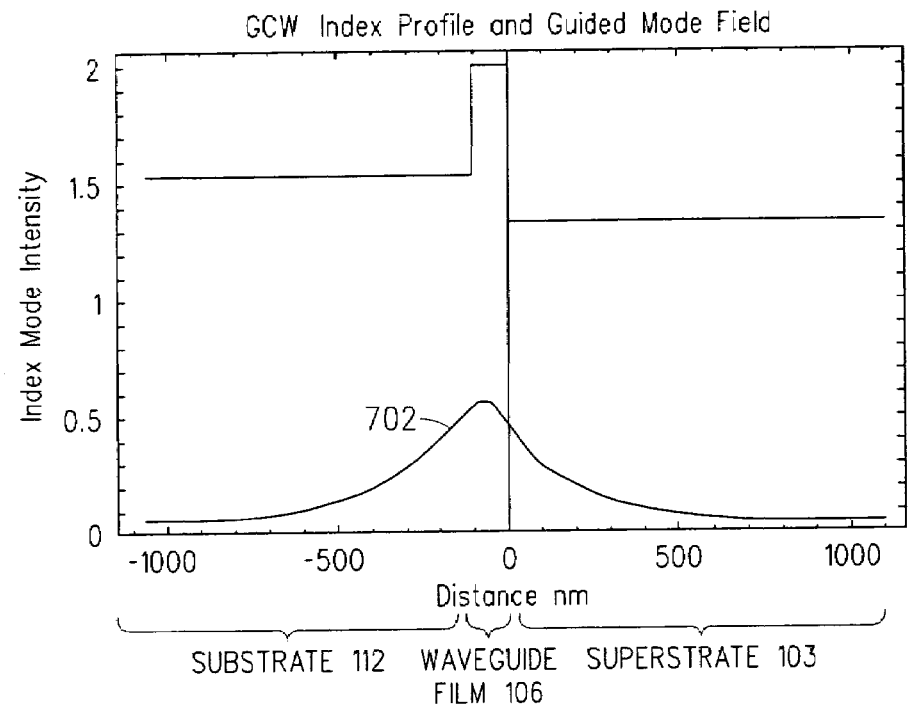
FIG. 7 (PRIOR ART) is a graph illustrating a fundamental mode which has an evanescent tail extending into a superstrate region of a traditional GCW that has a substrate made from cyclic-olefin copolymer (COC) (index $n_S=1.53$) a waveguide film made from $Ta_2O_5$ (index $n_f=2.01$) and a superstrate containing $H_2O$ (index $n_c=1.33$)

Referring to FIG. 7, there is a graph illustrating a fundamental mode 702 having an evanescent tail extending in the superstrate 103 of a traditional GCW that has a substrate 112 made from cyclic-olefin copolymer (COC) (index $n_S$=1.53), a waveguide film 106 made from $Ta_2O_5$ (index $n_f$=2.01) and a superstrate 103 containing $H_2O$ (index $n_c$=1.33). The fundamental TE mode 702 can be seen in FIG. 7 where the geometry of the GCW shown in FIG. 6 has been rotated 90° clockwise. The zero distance corresponds to the interface between the waveguide film 106 and the superstrate 103.

This graph shows the fundamental mode 702 of the waveguide 110 centered over the high-index waveguide film 106. Moreover, the fundamental mode 702 has an evanescent tail that extends further into the substrate 112 than into the superstrate 103 (cover/sensing region). This is a result of the index difference between the waveguide 110 and substrate 112. As mentioned above, the WIS/AIS are directly proportional to the area of the guided mode's evanescent tail that extends into the superstrate 103. By lowering the index of the substrate 112, the mode 702 confinement can be improved by forcing the mode effective index towards the superstrate 103 (see FIGS. 8 and 10).

The evanescent tail is the portion of the mode 702 outside of the waveguide 110. Technically, the evanescent tail is the portion of the mode 702 that exhibits exponential decay with distance. The field becomes evanescent when the effective index of the mode is greater than the local material index. In the exemplary GCW 100 shown in FIG. 6, the waveguide film 106 (central layer) is the only layer where the local index exceeds the mode effective index, so this is the only region where the field oscillates and acts like a conventional wave. In the surrounding layers 112 and 103, the mode index exceeds the local index, and the mode decays in intensity as it moves further from the waveguide layer 110. This decaying portion of the mode 702 extending some small distance into the surrounding region is termed the "evanescent tail" of the mode 702. Since the superstrate 103 is the top surrounding region and also where the biological reaction takes place, the evanescent tail of the mode 702 in this region is the portion of the mode 702 that does all of the biological sensing.

Figure 8:
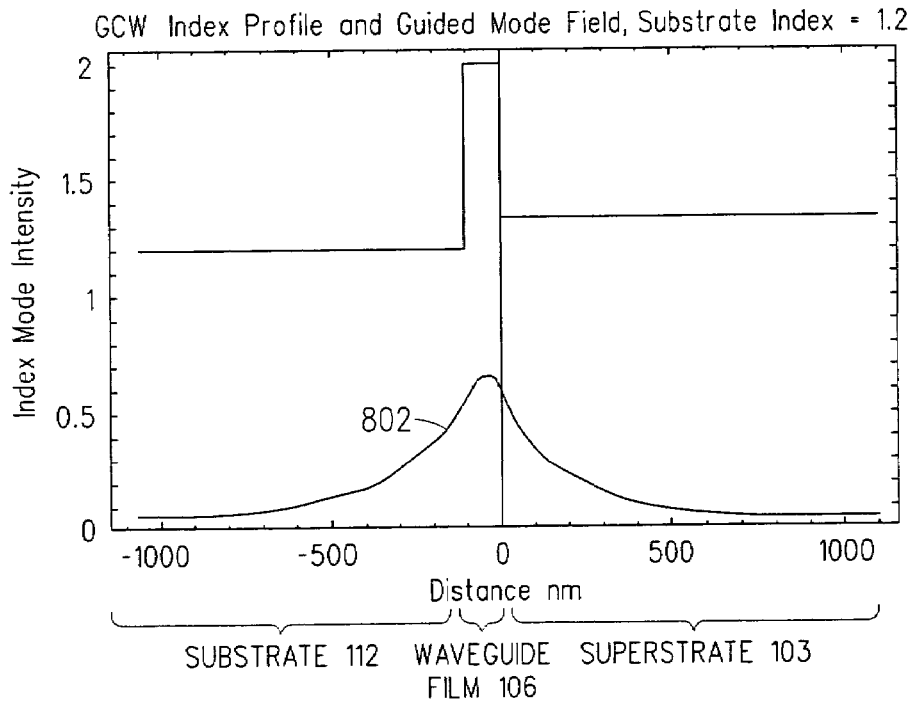
FIG. 8 is a graph illustrating a fundamental mode which has an evanescent tail extending into a superstrate region of an exemplary GCW that has a substrate with an index $n_S=1.20$, a waveguide film with an index $n_f=2.01$ and a superstrate with an index $n_c=1.33$.

Referring to FIG. 8, there is a graph illustrating a fundamental mode 802 which has an evanescent tail extending in a superstrate region 103 of an exemplary GCW 100 that has a substrate 112 with an index $n_S$=1.20, a waveguide film 106 with an index $n_f$=2.01 and a superstrate 103 with an index $n_c$=1.33. This graph clearly shows that the guided fundamental mode 802 extends further into the superstrate 103 thereby increasing the WIS/AIS when compared to the traditional GCW shown in FIG. 7.

Figure 9:
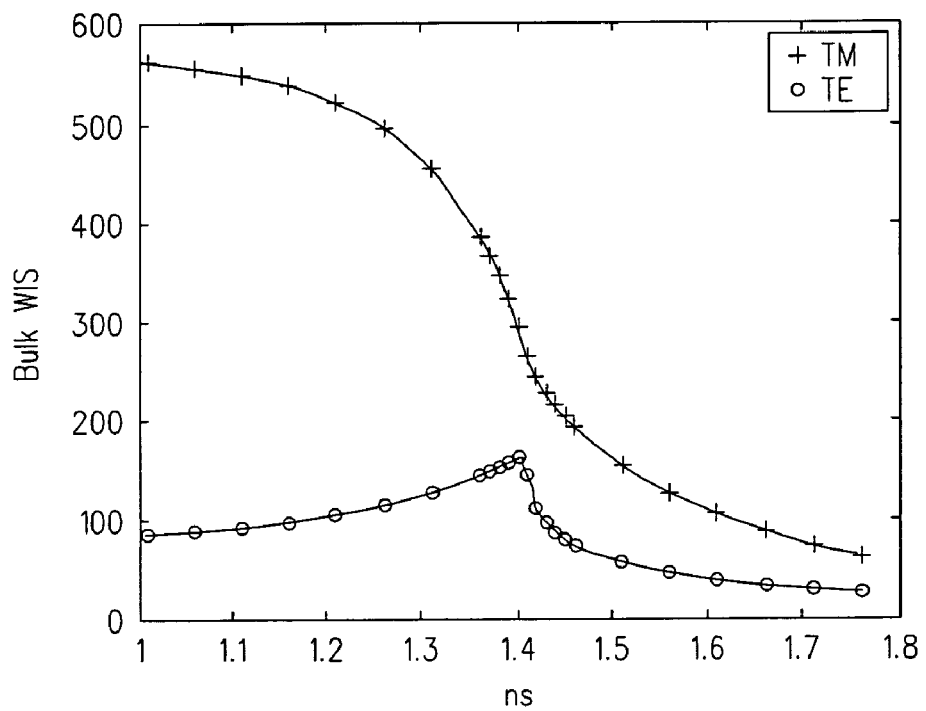
FIG. 9 is a graph that shows the result for both the TM fundamental mode and the TE fundamental mode of the waveguide in an exemplary GCW where the bulk sensitivity WIS is a function of the index of the substrate.

To quantify the resultant benefits of lowering the index of the substrate 112 as was done in the exemplary GCW 100 shown in FIG. 8, the index of the superstrate 103 was varied in the RCWA code while the resonance wavelength location was monitored. FIG. 9 shows the result for both the TM fundamental mode and the TE fundamental mode of the waveguide 110 where the bulk sensitivity WIS is a function of the index of the substrate 112 for a particular waveguide thickness. As can be seen, when the substrate 112 had an index of $n_S$=1.53 (see FIG. 7) then the TE sensitivity is ~50 and the TM sensitivity is ~130. But, as the index of the substrate 112 was lowered then the TM sensitivity could be as high as 550 which is a ~4-fold improvement while the TE sensitivity could peak near 175 which is also a ~4-fold improvement. It should be appreciated that the GCW 100 should be able to operate in either a TE or TM mode, and that the functionality will be different in each case. This results from the difference between the physical equations governing the electric and magnetic components of the fundamental mode. In the preferred embodiment, the GCW 100 would operate in the TM mode which would provide the most sensitive WIS/AIS, although most measurements made to date are using the TE mode since it provides a stronger and more easily detected signal.

Figure 10:
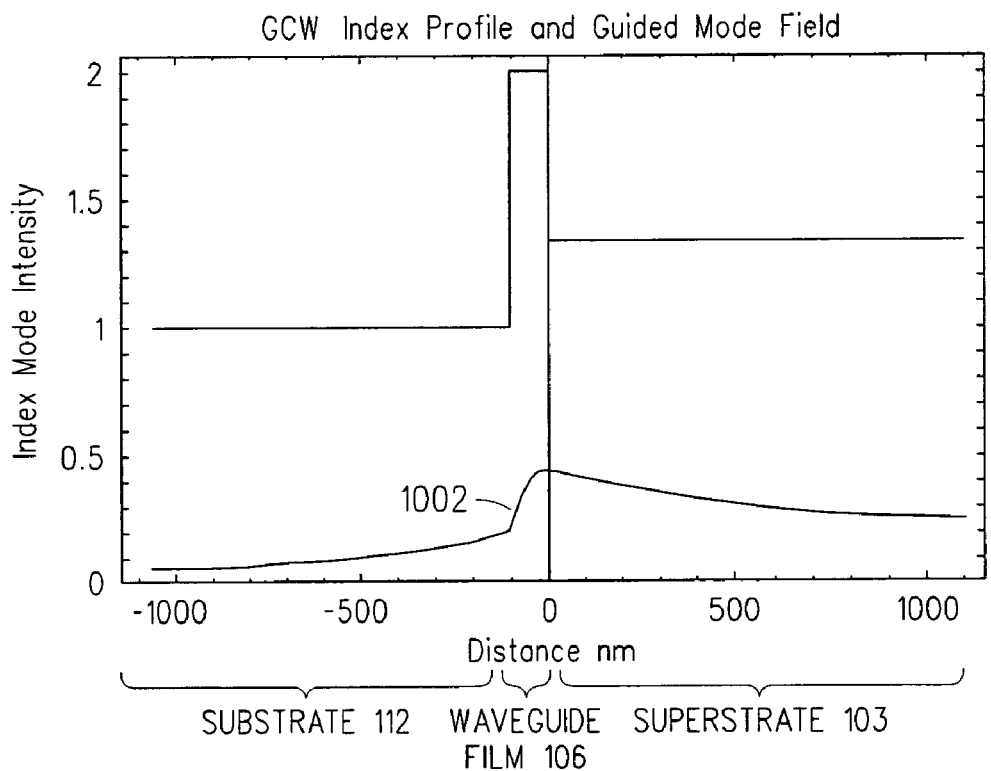
FIG. 10 is a graph illustrating a fundamental mode which has an evanescent tail extending into a superstrate region of an exemplary GCW that has a substrate with an index $n_S=1.00$, a waveguide film with an index $n_f=2.01$ and a superstrate with an index $n_c=1.33$.

The improvement in GCWs 100 that have substrates 112 with indexes $n_S \leq 1.5$ comes mainly from the elongation of the evanescent tail of the waveguide mode 802 into the superstrate 103. The longer the evanescent tail overlaps and "samples" the sensing region of the superstrate 103 the greater the sensitivity of the GCW 100. This effect becomes particularly pronounced when the mode 802 moves closer to cutoff by decreasing the index of the substrate 112. This extreme field penetration or cutoff can be seen in FIG. 10 which shows the index profile and fundamental mode 1002 of an exemplary GCW 100 that that has a substrate 112 with an index $n_s=1.00$, a waveguide film 106 with an index $n_f=2.01$ and a superstrate 103 with an index $n_c=1.33$. In this case, the evanescent tail length (1/e point) is 1.17 $\mu$m in the superstrate 103. This can be compared to a tail length of 161 nm when the substrate 103 has an index $n_s=1.53$ (see FIG. 7). It should be appreciated that the cutoff is a condition where the guided mode 1002 of the waveguide 110 is no longer guided; this can be caused by reduced index difference between the waveguide film 106 and either the substrate 112 or superstrate 103, or by a reduction in the thickness of the waveguide film 106, or both. FIG. 10 shows the case where the index of the substrate 112 starts to become so low relative to the waveguide film 106 that the mode 1002 is poorly confined at the interface of the waveguide film 106 and the superstrate 103. This causes the evanescent tail of the waveguide mode 1002 to penetrate further and further into the superstrate 103. This graph is a precursor to a fully cutoff mode, where the light would leak completely into the superstrate 103.

Another parameter that is important to consider in the design of the GCW 100 is the surface sensitivity as opposed to the bulk sensitivity (see FIG. 9). Because, a biologist may be interested in monitoring binding to the top surface 104 of the GCW 100 and as such it is important to have the ability to separate bulk response from surface response. Typically, an assay would include first measuring the response of the GCW 100 with a buffer (pure water) at the surface 104, next the GCW 100 would be exposed to some biological substance 102 in a fluid thereby allowing some material 102 to bind to the surface 104, and finally rinsing the remaining biological fluid 102 from the GCW 100 with replacement buffer. The difference between the initial and final response of the GCW 100 with the buffer at the surface 104 would then indicate the net index change due to the binding of the biological substance 102 to the surface 104. In this case, it becomes apparent that the response of the GCW 100 to the bulk medium would be subtracted, leaving only the surface contribution. It should be readily appreciated that the "surface" is considered to be the first ~100 nm above the top surface 104 of the GCW 100, as this is the typical sensing range of current commercial instrumentation (surface plasmon resonance equipment, for example), and represents a distance of ~few monolayers of biological materials 102 for many typical assays.

Figure 11:
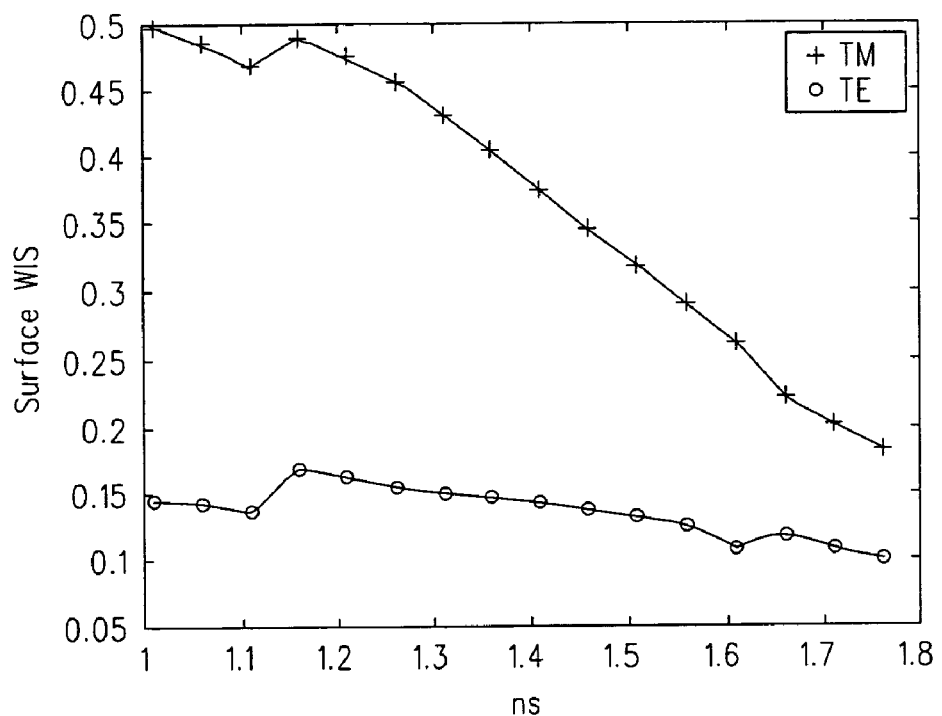
FIG. 11 is a graph that shows the result for both the TM fundamental mode and the TE fundamental mode of the waveguide in an exemplary GCW where the surface sensitivity WIS is a function of the index of the substrate.

To describe how the GCW 100 with a particular waveguide thickness responds to surface index changes as opposed to bulk surface fluids, the above sensitivity calculations can be revisited, where only a 1 nm layer above the top surface 104 of the GCW 100 is allowed to vary in index, while the covering bulk fluid is held constant (see FIG. 11). This thickness is somewhat arbitrary but arguably confines effects to the surface 104 and since all sensitivities are relative measures, this choice of study distance should not limit the scope of this invention. Moreover, lengthening the distance of the surface 104 has been shown to have no impact on the findings so long as the thickness remains substantially less than the evanescent tail length.

Referring to FIG. 11, there is a graph that shows the result for both the TM fundamental mode and the TE fundamental mode of the waveguide in the GCW 100 where the surface sensitivity WIS is a function of the index of the substrate 112. As can be seen, this graph indicates that there is a much smaller improvement in the surface sensitivity of the GCW 100 when the index of the substrate 112 is lowered when compared to the marked improvement in the bulk sensitivity (see FIG. 9). This can be explained by considering the graph shown in FIG. 10 and the discussion of the deeply penetrating evanescent tail for a small substrate index; much of the benefit of improved bulk sensitivity shown in FIG. 9 results from the massive extension of the guided mode's evanescent tail into the bulk fluid in the superstrate 103. This will greatly enhance bulk sensitivity while minimally affecting surface sensitivity. Nonetheless, the graph in FIG. 11 confirms that lowering the index of the substrate 112 still has positive implications for surface sensitivity: an increase of ~28% moving from $n_s=1.50$ to $n_s=1.35$.

Even though these theoretical results indicate a relatively small improvement in the surface sensitivity of GCWs 100 when the substrate 112 has an index $n_S \leq 1.5$, the experimental results described below indicate that the improvement is actually much larger by nearly 200%. Moreover, even if the surface sensitivity improvement is smaller than the bulk sensitivity, one should keep in mind that biological consumers also care about bulk index changes under certain circumstances such as studying larger molecules and/or cells, for example. As such, the lowered substrate index GCWs 100 would enable a product to target this market due to the extreme field penetration into the superstrate 103, where traditional surface-optimized DBA products would be completely insensitive.

Following is a discussion about some of the different materials that can be used to make the low index substrate 112 in the GCW 100. And, since GCWs 100 used in biosensing applications often have the requirement of being a low-cost item, plastic materials are preferable since often the raw materials are inexpensive and plastics are easily microreplicated. From the calculations made above with respect to FIGS. 6–11, it is apparent that the required substrate material should have an index of refraction lower than approximately 1.5.

For example, materials that can be used to make the substrate 112 which have refractive indexes between 1.4–1.5 includes several thermoplastic materials, polyvinylidene fluoride (PVDF), polymethylpentene (PMP), or blends of PVDF/polymethylmethacrylate (PMMA). To further enhance the effect of the lower index substrate, the material used to make the substrate 112 preferably would have an index below ~1.4. One class of "speciality" materials that has an index below ~1.4 includes optical grade fluoropolymers. Another example of a "specialty" material that can be used includes a perfluoro-polymer manufactured by Asahi which is injection moldable. Yet another example of a possible "specialty" material that can be used is DuPont's Teflon AF. There are also several fluoropolymers which can be used that are cured through exposure to UV light to form the low index substrate 112 and diffraction grating 108. One such example is a fluoroacrylate which has a refractive index of ~1.35.

In a set of experiments, the inventors prepared exemplary waveguides 110 from one variety of these materials, namely UV 110. The process was as follows:

1) A glass substrate was cleaned and treated with an adhesion promoter.

2) A syringe was used to dispense a very small amount of material 112 (~300 $\mu$L).

3) The substrate 112 was suspended above a grating "pill" with spacer (~0.2 mm).
4) The sample 112 was placed in a purge box and purged with nitrogen for ~30 seconds.
5) The sample 112 was exposed for 10 seconds to 120 mJ/cm^2 @365 nm.
6) The grating master was removed and the sample 112 was coated with a 140 nm $Ta_2O_5$ waveguide film 106.

An angular interrogation scheme was used to test these samples and the experimental results are discussed below. In these experiments, the waveguide resonance was monitored as a function of the cover index to obtain a bulk AIS, and a subsequent electrostatic layer experiment helped to obtain the surface sensitivity. In order to determine the benefit of the low-index substrate 112, a "regular" cyclic-olefin copolymer (COC) substrate (n~1.52) GCW was compared under the same experimental conditions with no adjustment of optics for both surface and bulk sensitivity.

Figure 12:
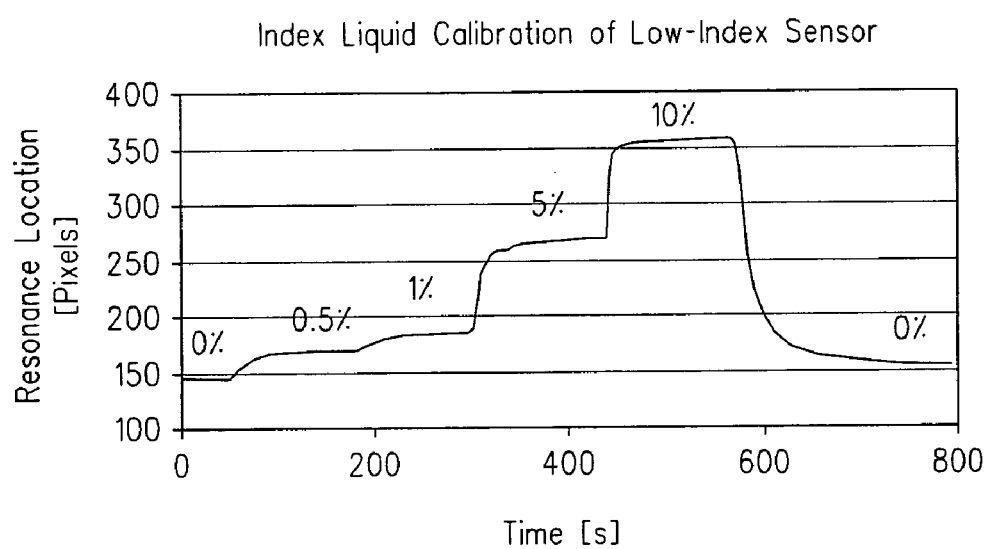
FIG. 12 is a graph that shows an example of the calibration data that can be used to determine the bulk sensitivity of a traditional GCW and the low-index substrate GCW shown in FIG. 1.

Bulk index fluids were prepared as a dilution series of glycerin and deionized water; glycerin concentrations of 0.5%, 1%, 2.5%, 5%, 10% were typically employed. According to the angular interrogation method, a single-wavelength laser 122 was used to excite the resonance and the angular position of the reflected resonance peak was monitored with a CCD camera 126 as a function of time, as these different index solutions were brought into contact with the traditional GCW and the low-index GCWs 100 (see also FIG. 1). FIG. 12 is a graph that shows an example of the calibration data used to determine the sensitivity of the traditional GCW and the low-index GCWs 100. This graph contains data on the amount of signal shift experienced when different refractive index fluids are placed into contact with the traditional GCW and the low-index GCWs 100. The different bulk fluids have well-known (calibrated) refractive indices, meaning that one can calculate a figure of merit: signal shift per refractive index unit. For example, water (0% solution) has an index of 1.333, whereas 5% (glycerol) solution has an index of 1.3336, and so on. The difference in signal (resonance location) for each of these solutions, divided by the index difference (0.0006) gives the sensitivity. And, by condensing the plateau data from such plots, the bulk sensitivities of the traditional GCW and the low-index GCWs 100 were calculated to be 5419 and 19395 pixels/RIU, indicating a 3.6x improvement in bulk sensitivity with the low-index GCWs 100.

Figure 13:
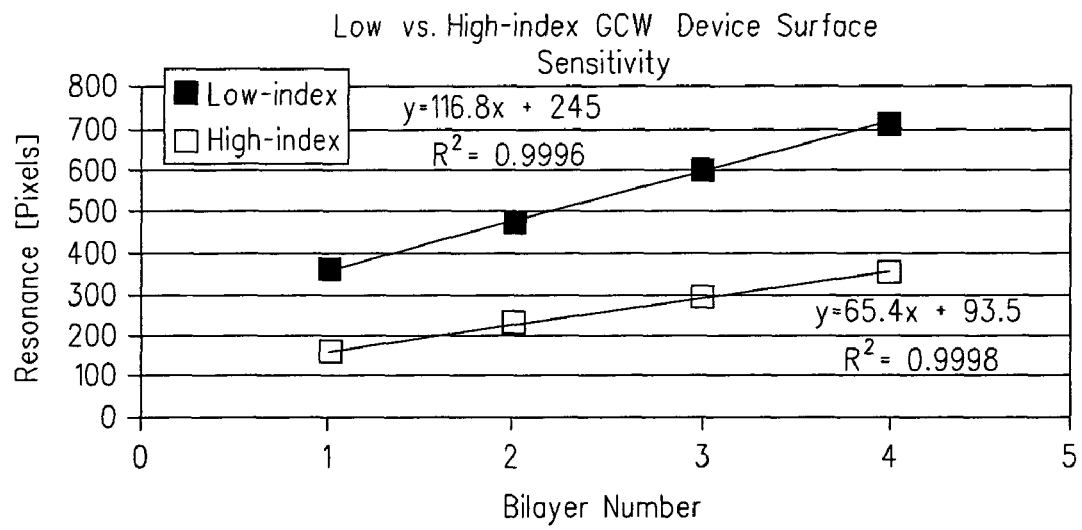
FIG. 13 is a plot of the optical response to the addition of successive bilayers of biological material to a traditional GCW and the low-index GCW shown in FIG. 1.

The surface sensitivity was determined by building successive electrostatically charged polymer monolayers that are ~4 nm on the surfaces 104 of the GCWs 100. A PSS (polystyrene sulfonate)/PAH (polyallyamine hydrochloride) system was used for this purpose which has been studied extensively, with commercial instruments as well as conventional metrology (e.g., ellipsometry). Together with monolayer density and molecular weight information, the ultimate surface response of the GCWs 100 in terms of molecular weight can thereby be determined. FIG. 13 is a plot of the optical response caused by adding successive bilayers of biological material 102 to both traditional GCWs and the low-index GCWs 100. The data (line slope) shows the GCW 100 having the low-index substrate to be 1.8x more sensitive than the traditional GCW which has the high-index substrate. While this is contrary to the modeling results associated with the theoretical modeling done with respect to FIG. 11, the result is repeatable, indicating a near 2x increase in surface sensitivity each time. A possible explanation for this improvement is due to the fact that the biological material 102 is adsorbed to the sides of the teeth in the diffraction grating 108 which changes the thickness of the gratings and in turn changes the duty cycle and effective index of the waveguide.

In another embodiment of the present invention, an array the GCWs 100 may be incorporated within the bottoms of wells 1402 formed within a frame of a microplate 1404 as shown in FIGS. 14A–14F. An exemplary process that can be used to incorporate the GCWs 100 into the bottoms of the wells 1402 in a microplate 1404 starts with dipping a dispensing tool 1406 into a low index UV curable liquid 1408 (e.g., fluoropolymers, fluoroacrylates). By adjusting the diameter of the extensions 1410 protruding from dispensing tool 1406, the volume of the liquid 1408 extracted can be precisely controlled (see FIG. 14A). The dispensing tool 1406 is then positioned above a grating tool 1412 (see FIG. 14B). Approximately 50% of the liquid 1408 on the dispensing tool 1406 is transferred to the surface of extensions 1414 protruding from the grating tool 1412 (see FIG. 14C). The grating tool 1412 is then brought into contact with the microplate 1404 (or alternatively, a flat substrate plate bottom for a two-part microplate), purged with nitrogen, and exposed to UV-curing radiation to turn the liquid 1408 into the substrate 112 (see FIG. 14D). The grating tool 1412 is then separated from the microplate 1404 (see FIG. 14E). At this point, the wells 1402 in the microplate 1404 have a relatively thick substrate 112 with a relatively small diffraction grating 108 impressed therein. Lastly, the waveguide film 106 is applied onto the diffraction grating 108 to form the GCWs 100 (see FIG. 14F). It should be appreciated that this process can reduce the amount of polymer used to produce a microplate and hence reduce cost.

Figure 15:
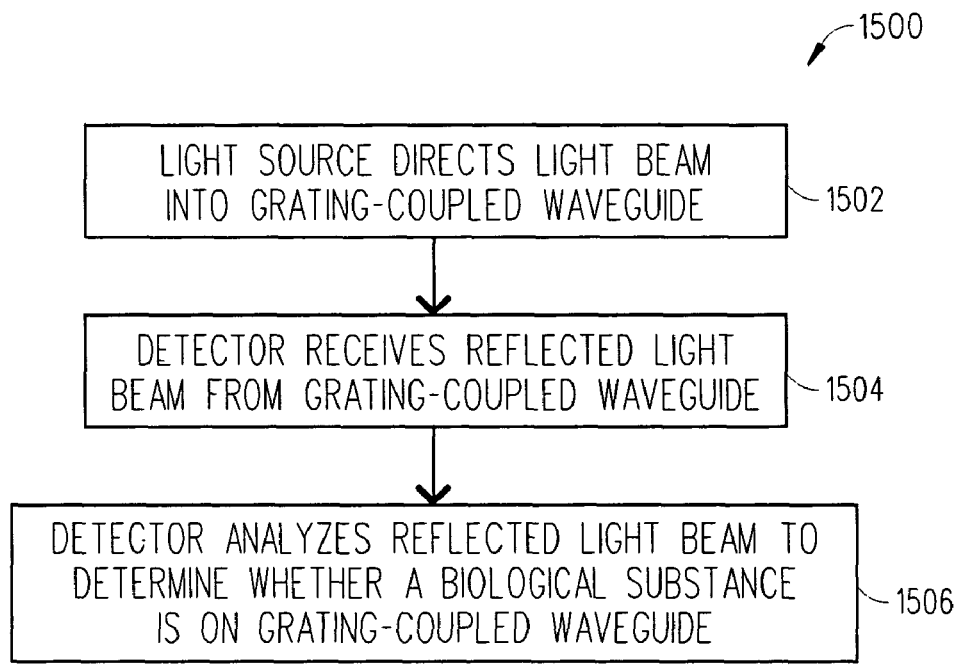
FIG. 15 is a flowchart illustrating the basic steps of a preferred method for using the optical interrogation system and the GCW shown in FIG. 1 to detect a biological substance in accordance with the present invention.
Figure 14A:
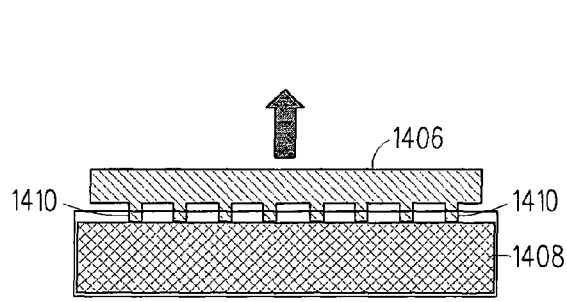
FIGS. 14A–14F illustrate the different steps in a manufacturing process for forming an array of GCWs within the bottoms of wells in a microplate.
Figure 14B:
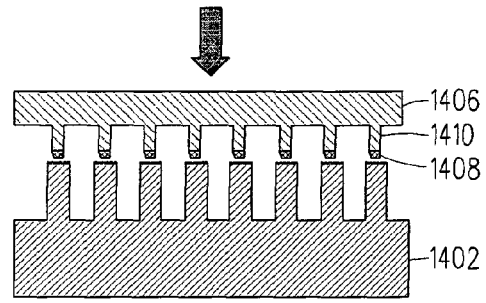
Figure 14C:
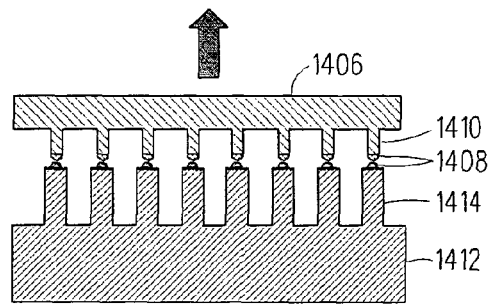
Figure 14D:
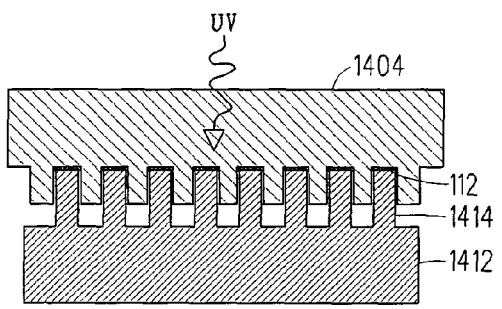
Figure 14E:
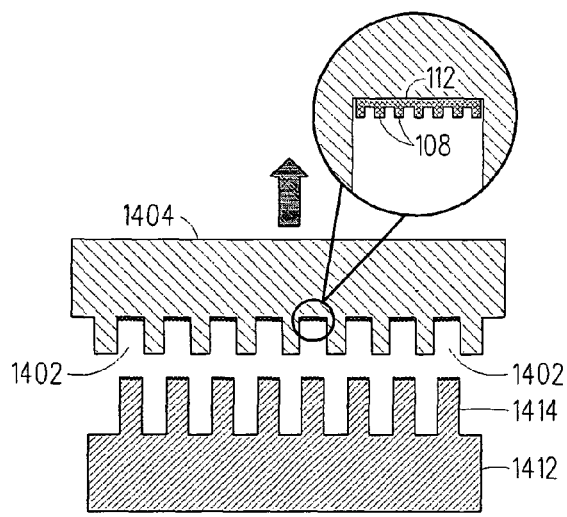
Figure 14F:
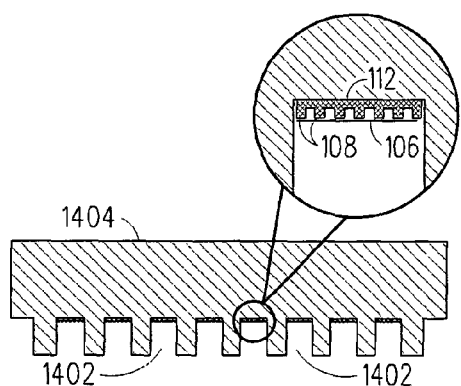

Referring to FIG. 15, there is a flowchart illustrating the basic steps of a preferred method 1500 for using the optical interrogation system 120 and the GCWs 100 to detect a biological substance 102 in accordance with the present invention. Although the GCWs 100 and optical interrogation system 120 are described herein as being used to detect the presence of biological substances 102 like cells, molecules, proteins, drugs, chemical compounds, nucleic acids, peptides or carbohydrates on the surfaces 104 of the GCWs 100, it should be understood that the GCWs 100 and optical interrogation system 120 can be used to perform a wide variety of studies. For example, the GCWs 100 and optical interrogation system 120 can be used to perform cell migration assays, drug permeability assays, drug solubility studies, virus detection studies and protein secretion studies.

Beginning at step 1502, the light source 124 is used to direct light beam(s) 126 into the GCW(s) 100. At step 1504, the detector 124 receives the reflected light beam(s) 128 from the GCW(s) 100. In one embodiment, the reflected light beams 128 may be multiplexed and input into the detector 124 (e.g., spectrometer). Then at step 1506, the detector 124 analyzes each of the received reflected light beams 128 to detect a resonant wavelength or resonant angle which corresponds to a predetermined refractive index that indicates whether the biological substance 102 is located in the superstrate 103 of the respective GCW 100. Each GCW 100 includes a substrate 112, a diffraction grating 108 and a waveguide film 106 that has a higher index of refraction than the substrate 112 which has an index of refraction $\leq 1.5$. As described above, the substrate 112 has a bottom surface that receives the light beam 126 which interfaces with a waveguide 110 formed by the diffraction grating 108 and the waveguide film 106 and diffracts into a fundamental mode which has an evanescent tail that extends further into the superstrate 103 (sensing region) above the waveguide film 106 than it would with a traditional substrate 103, because the substrate 103 has an index of refraction≦1.5. The fact that the evanescent tail extends further into the sensing region 103 leads to an increase in the sensitivity of the GCW 100.

Following are some advantages and uses of the GCWs 100 and optical interrogation system 120 of the present invention:

The concept of using a low-index substrate 112 in a GCW 100 has been shown herein to change the guided field distribution in the structure of the GCW 100. This change allows the field to better penetrate the superstrate 103 of the GCW 100, thereby increasing the GCW's sensitivity to surface index changes. This increase in sensitivity greatly enhances the performance of the GCW 100 as well as relaxing requirements on the optical system 120 used to decode the response of the GCW 100 to a given index sensitivity specification.

The concept of lowering the index of the substrate 112 can be applied to a wide class of sensors that have similar designs, and can be used to increase the sensitivity of sensors without significant changes to the process tooling and fabrication.

It should be appreciated that although the index of the waveguiding film 106 affects the overall optimization and physical parameters (e.g., material and chemical compatibility between the different layers, ease of processing, storage issues) of the GCW 100 it is the lowering of the index of the substrate 112 that causes the increase to the sensitivity of the GCW 100. In particular, as one varies the index of the waveguide film 106 this changes the "average" optical mode confinement, while varying the index of the substrate 112 changes the mode symmetry to determine whether the mode is mostly in the substrate 112 or superstrate 103. It has been assumed herein that the index of the superstrate 103 cannot be changed appreciably since most biological reactions are performed in a water solution.

It should be appreciated that the index of substrate 112 is best compared to the index of the superstrate 103 to determine the efficacy of the invention. One should try to avoid the situation where the substrate 112 has a much higher index than the index of the superstrate 103.

It should be note that if one is interested in what happens at the sensor surface (i.e. within a couple hundred nm of the surface), then extending the evanescent tail too deeply into the superstrate 103 can actually increase the signal from the "bulk" solution relative to the surface contribution. As a result, one should balance the pushing of the evanescent tail further into the substrate 103 and favoring the surface signal.

It should be appreciated that the interrogation instrument is not limited to working with the reflected signal. In addition, the interrogation instrument can work with waveguide coupled light (peak) or transmitted light (dip).

It should be appreciated that although the waveguide film 106 is shown as planarising in FIG. 1, it more likely is conformal to the underlying diffraction grating 108 while maintaining a fairly uniform film thickness.

Although the preferred embodiment of the present invention described above utilized a reflected light beam to enable the detection of the biological substance, it should be readily appreciated that a transmitted beam and even a beam exiting the side of the sensor could also be used to detect the biological substance. Of course, minor changes to the set-up of the system would be required to detect the transmitted beam or the beam exiting the side of the sensor.

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A grating-coupled waveguide comprising:
   a substrate;
   a diffraction grating; and
   a waveaulde film that has a higher index of refraction than said substrate which has an index of refraction≦1.5, wherein said substrate is a thermoplastic material including at least one of a polyvinylidene fluoride, polymethylpentene and blends of polyvinylidene fluoride/polymethylmethacrylate.

2. A grating-coupled waveguide comprising:
   a substrate;
   a diffraction grating; and
   a waveguide film that has a higher index of refraction than said substrate which has an index of refraction≦1.5, wherein said substrate is a fluoropolymer including fluoroacrylate.

3. The grating-coupled waveguide of claim 2, wherein said substrate has an index of refraction≦1.4.

4. A grating-coupled waveguide comprising:
   a substrate;
   a diffraction grating;
   a waveguide film formed above said substrate, wherein said waveguide film has a higher index of refraction than said substrate which is a thermoplastic material that has an index of refraction≦1.5;
   wherein said diffraction grating is either fabricated directly into said substrate or said waveguide film, or located in optical proximity to the said waveguide film, or formed within said waveguide film itself; and
   wherein said substrate has a bottom surface that receives a light beam which interfaces with a waveguide formed by said diffraction grating and said waveguide film and diffracts into a fundamental mode which has an evanescent tail that extends into a sensing region located above said waveguide film.

5. The grating-coupled waveguide of claim 4, wherein a surface sensitivity in the sensing region above said waveguide film is enhanced because said substrate has an index of refraction≦1.5.

6. The grating-coupled waveguide of claim 4, wherein a bulk sensitivity in the sensing region above said waveguide film is enhanced because said substrate has an index of refraction≦1.5.

7. The grating-coupled waveguide of claim 4, wherein said substrate has an index of refraction inthe range of about 1.4–1.5.

8. A grating-coupled waveguide comprising:
   a substrate;
   a diffraction grating;
   a waveguide film formed above said substrate, wherein said waveguide film has a higher index of refraction than said substrate which has an index of refraction≦1.5;

wherein said diffraction grating is either fabricated directly into said substrate or said waveguide film, or located in optical proximity to the said waveguide film or formed within said waveguide film itself;

wherein said substrate has a bottom surface that receives a light beam which interfaces with a waveguide formed by said diffraction grating and said waveguide film and diffracts into a fundamental mode which has an evanescent tail that extends into a sensing region located above said waveguide film; and wherein said substrate is a thermoplastic material including at least one of a polyvinylidene fluoride, polymethylpentene and blends of polyvinylidene fluoride/polymethylmethacrylate.

9. A grating-coupled waveguide comprising:

a substrate;

a diffraction grating;

a waveguide film formed above said substrate, wherein said waveguide film has a higher index of refraction than said substrate which has an index of refraction $\leq 1.5$;

wherein said diffraction grating is either fabricated directly into said substrate or said waveguide film, or located in optical proximity to the said waveguide film, or formed within said waveguide film itself;

wherein said substrate has a bottom surface that receives a light beam which interfaces with a waveguide formed by said diffraction grating and said waveguide film and diffracts into a fundamental mode which has an evanescent tail that extends into a sensing region located above said waveguide film; and wherein said substrate is a fluoropolymer including fluoroacrylate.

10. The grating-coupled waveguide of claim 9, wherein said substrate has an index of refraction $\leq 1.4$.

11. A grating-coupled waveguide comprising:

a substrate;

a diffraction grating; and a waveguide film that has a higher index of refraction than said substrate which is a fluoropolymer that has an index of refraction $\leq 1.4$.

12. The grating-coupled waveguide of claim 11, wherein said fluoropolymer is a fluoroacrylate.

* * * * *